US00PP28728P3

(12) United States Plant Patent
Lee

(10) Patent No.: US PP28,728 P3
(45) Date of Patent: Dec. 5, 2017

(54) ***RHODODENDRON* PLANT NAMED 'BAILEB'**

(50) Latin Name: ***Rhododendron* hybrid**
Varietal Denomination: BAILEB

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 48 days.

(21) Appl. No.: 14/998,401

(22) Filed: Dec. 31, 2015

(65) Prior Publication Data

US 2017/0196143 P1 Jul. 6, 2017

(51) Int. Cl.
*A01H 5/02* (2006.01)

(52) U.S. Cl.
USPC ..... Plt./239

(58) Field of Classification Search
USPC ..... Plt./238, 239, 240
See application file for complete search history.

*Primary Examiner* — June Hwu
(74) *Attorney, Agent, or Firm* — Cassandra Bright

(57) ABSTRACT

A new and distinct *Rhododendron* cultivar named 'BAILEB' is disclosed, characterized by distinctive semi-double red-purple flowers dotted darker red-purple. Plants bloom Spring, Summer and Fall and exhibit good tolerance for hot conditions and other environmental stressors. Plants are easy to propagate and have very dark green foliage, near RHS Green 139A. The new cultivar is a *Rhododendron*, suitable for ornamental garden purposes.

2 Drawing Sheets

Figure 1:
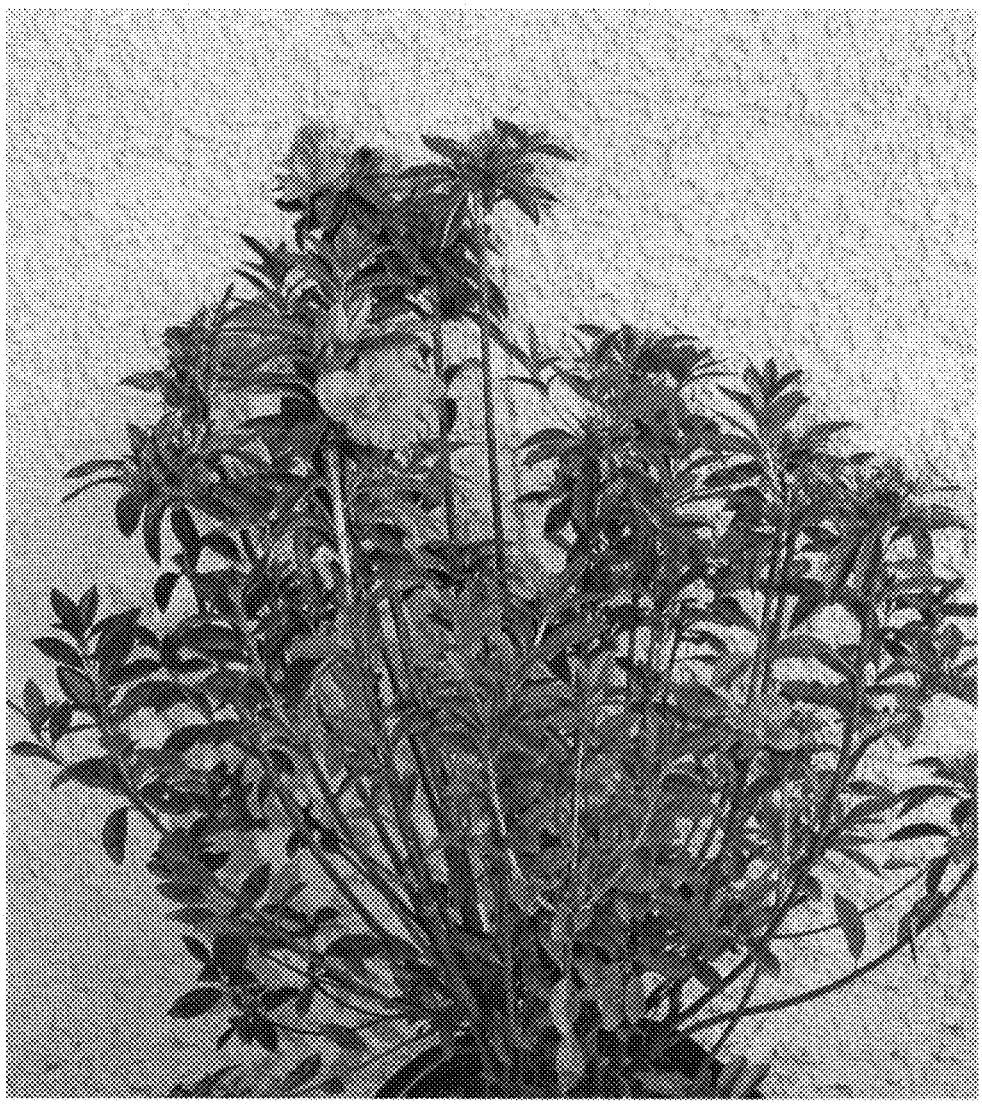

Latin name of the genus and species: *Rhododendron* hybrid.

Variety denomination: 'BAILEB'.

BACKGROUND OF THE INVENTION

The new cultivar is a product of a planned breeding program by the inventor, Robert Edward Lee. The inventor's intention was to develop *Rhododendron* hybrid plants with re-blooming characteristics. This new variety, hereinafter referred to as 'BAILEB', was discovered as a seedling, resulting from the crossing of *Rhododendron* 'Schroeder's Pink Perfection', unpatented with the pollen parent *Rhododendron olhamii* 'Fourth of July', unpatented. The cross resulting in the new variety occurred during the Spring of 1990. The new variety was selected by the inventor during the Fall of 1996 at a commercial nursery in Independence, La.

After identifying the new variety as a potentially interesting selection, the inventor first organized propagation of 'BAILEB' by vegetative terminal cuttings Fall of 1996 at the same commercial nursery in Independence, La. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'BAILEB' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BAILEB' These characteristics in combination distinguish 'BAILEB' as a new and distinct *Rhododendron* cultivar:

1. Unique Spring, Summer, and Fall blooming.
2. Flowers colored near RHS Red-Purple 68A upper petals dotted with Red-Purple 67A.
3. Dark green mature leaf color near Green 139A.
4. Tolerant of environmental stressors.
5. Good heat tolerance.
6. Plants well suited for landscape use, including as a specimen plant or hedge.
7. Observed hardy to at least Zone 7.
8. Easy propagation

COMPARISON TO PARENT VARIETY

'BAILEB' is similar in most horticultural characteristics to the seed parent. *Rhododendron* hybrid 'Schroeder's Pink Perfection'. Plants of the new cultivar 'BAILEB' however differ in the following:

1. The new variety has a darker red-purple flower color.
2. Flowers of the new variety are larger.
3. Plants of the new variety grow larger, approximately double in size after 10 years, compared to plants of this comparator.

'BAILEB' is similar in most horticultural characteristics to the pollen parent *Rhododendron olhamii* 'Fourth of July'. Plants of the new cultivar 'BAILEB' however differ in the following:

1. 'BAILEB' produces semi-double flower, flowers of 'Fourth of July' are single.
2. The new variety has a red-purple flower, whereas flower color of 'Fourth of July' is brick red with a purple blotch.
3. The new variety tolerates lower temperatures.
4. Plants of the new variety are more vigorous.
5. Plants of the new variety have a stronger root system.

COMMERCIAL COMPARISON

'BAILEB' can be compared to the commercial variety *Rhododendron* hybrid 'Roblec' U.S. Plant Pat. No. 15,339. Plants of the new cultivar 'BAILEB' are similar to plants of 'Roblec' in most horticultural characteristics, however, plants of the new cultivar 'BAILEB' differ in the following:

1. 'Baileb' has a lighter red-purple flower.
2. Plants of 'Baileb' grow more slowly than plants of 'Roblec'.
3. Mature foliage of 'Baileb' is dark green, near RHS Green 139A, mature foliage of 'Roblec' is Yellow-Green 147A.

'BAILEB' can be compared to the commercial variety *Rhododendron* hybrid 'Conlea' U.S. Plant Pat. No. 10,438. Plants of the new cultivar 'BAILEB' are similar to plants of 'Conlea' in most horticultural characteristics, however, plants of the new cultivar 'BAILEB' differ in the following;

1. 'Baileb' has lighter colored flowers than 'Conlea'.
2. Foliage of 'Conlea' is smaller.
3. Foliage of the new variety is darker green than foliage of 'Conlea'.

BRIEF DESCRIPTION OF THE PHOTOGRAPH

The accompanying photograph in FIG. 1 illustrates in full color a 2 year old plant of the new variety in a 3 gallon pot.

Figure 2:
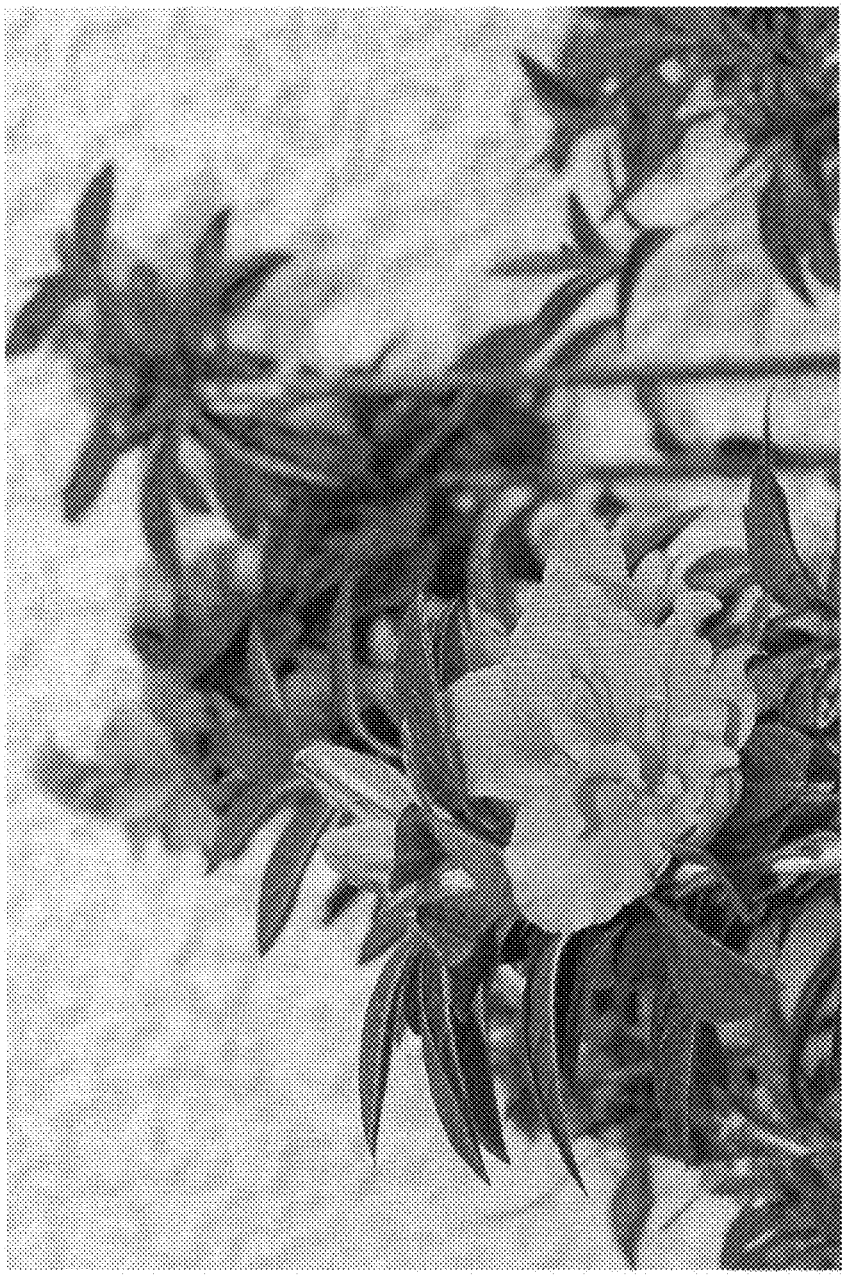

FIG. 2 illustrates in full color a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BAILEB' plants grown outdoors in Loxley, Ala. Plants are approximately 2 years old, in a 3 gallon nursery container. Measurements and numerical values represent averages of typical plant types.

Botanical classification: *Rhododendron* hybrid 'BAILEB'.

PROPAGATION

Typically by semi-hardwood cuttings in Spring and Summer.

Root description: Fine, fibrous young roots, well branched. Colored near RHS Grey-Brown 199A.

PLANT

Growth habit: Upright evergreen shrub.

Height: Approximately 75 cm to top of foliar and flowering plane.

Plant spread: Approximately 60 cm.

Branching characteristics: Moderately well branched, approximately 3 to 4 primary branches from the center of the plant. Branches occur at approximately 15° angles. Each primary branch has 4 to 8 lateral branches.

Primary branches:

Length of primary branches: Primary branches are pinched, remaining at approximately 10 cm.

Diameter of primary branches: Approximately 1.4 cm.

Primary branch strength: Very strong, difficult to break.

Primary branch color: Near Greyed-Orange 175A, completely covered with an overlay color near Green 137B.

Primary branch texture: Slightly rough, minor peeling or scaly texture.

Lateral branches:

Number of lateral branches: Approximately 4 to 8 per primary branch.

Length of lateral branches: Average range 40 to 55 cm.

Diameter of lateral branches: Average 0.8 cm.

Lateral branch strength: Very strong, flexible.

Lateral branch color: New growth near RHS Yellow-Green 151A; oldest branches become woody, colored near Greyed-Orange 177A.

Lateral branch texture: Immature growth hirsute. Older growth somewhat rough, slightly, hirsute.

Internode length: Average range 3.0 cm to 5.0 cm.

Age of plant described: Approximately 2 years.

FOLIAGE

Leaf:

*Type*.—Simple.

*Arrangement*.—Sub-opposite.

*Average length*.—Approximately 5.5 cm.

*Average width*.—Approximately 1.8 cm.

*Shape of blade*.—Elliptic.

*Apex*.—Acute.

*Base*.—Attenuate.

*Attachment*.—Stalked.

*Margin*.—Entire. Short cilliate.

*Texture of top surface*.—Moderately pubescent. Hairs appressed, very short, rough.

*Texture of bottom surface*.—Moderately pubescent. Hairs short, rough.

*Color*.—Young foliage upper side: Near RHS Yellow-Green 144A, slightly darker. Young foliage under side: Near RHS Yellow-Green 146C. Mature foliage upper side: Near RHS Green 139A. Mature foliage under side: Near RHS Yellow-Green 146B.

*Venation*.—Type: Pinnate. Venation color upper side: Near RHS Yellow-Green 152D. Venation color under side: Near RHS Yellow-Green 151B.

*Petiole*.—Length: About 0.7 cm. Diameter: About 0.15 cm. Color: Upper Surface: Near RHS Yellow-Green 152B. Lower Surface: Near RHS Yellow-Green N144A.

FLOWER

Bloom period: Plants begin flowering in the Spring, and continue to produce flowers throughout Summer and Fall.

Flower:

*Arrangement*.—Axillary clusters of perfect, open funnel shaped individual flowers. Typically 5 to 9 flowers per cluster.

*Lastingness*.—Individual flowers last approximately 2 weeks, each bloom period lasts approximately 4 to 6 weeks.

Inflorescence:

*Height*.—Average 9.0 cm.

*Diameter*.—Average 12.0 cm.

Peduncle: Not present, inflorescence pedicels emerge directly from node.

Pedicel:
*Length*.—Average 0.8 cm to 1.7 cm.
*Diameter*.—0.3 cm.
*Color*.—Near RHS Red-Purple 61C.
*Texture*.—Densely pubescent. Long, soft hairs colored near White N155B.
*Aspect*.—Slightly curved. Angle of attachment, approximately 45° to 75° angle from stem.
*Strength*.—Sturdy and flexible.

Flowers:
*Length*.—Average 4.0 cm.
*Diameter*.—Average 6.0 cm.
*Facing direction*.—Outwardly and upwardly facing.
*Persistent or self-cleaning*.—Corolla self-cleaning.
*Fragrance*.—Faint sweet scent.

Tube:
*Tube length*.—Approximately 1.5 cm.
*Tube width a widest point*.—Approximately 1.7 cm.
*Tube width and narrowest point*.—Approximately 0.6 cm.

Petals:
*Unfused petal segments*.—
*Length*.—Approximately 2.7 cm.
*Width*.—Approximately 2.1 cm
*Apex*.—Blunt, rounded.
*Shape of petal*.—Unfused portion, oblong.
*Petal margin*.—Entire. Aspect undulating to ruffled.
*Petal arrangement*.—Overlapping, bilateral symmetry dissecting bottom petal. Petals fused approximately ⅓ distance from base.
*Petal number*.—Average range 6 to 8.
*Petal texture*.—Smooth.
*Color*.—Upper surface at first opening: Near RHS Red-Purple N66C. Dotted near Red-Purple 53B. Under surface at first opening: Near RHS Red-Purple N66B. Inner surface at maturity: Near RHS Red-Purple 68A upper petals dotted with Red-Purple 67A. Outer surface at maturity: Near RHS Red-Purple 68B. Upper surface at fading: Near RHS Red-Purple 68A upper petals dotted with Red-Purple 70A. Under surface at fading: Near RHS Red-Purple 70B. Interior Corolla tube: Near RHS Red-Purple 73D, with moderate quantity of throat markings near 59A. Exterior Corolla tube: Near RHS Red-Purple 68B.

Petaloids:
*Quantity*.—About 4 to 6.
*Length*.—Average range 1.3 to 2.1 cm.
*Width*.—Average range 1.0 to 1.4 cm
*Apex*.—Irregularly rounded.
*Shape*.—Irregular ovoid.
*Margin*.—Entire. Moderately undulating to ruffled.
*Texture*.—Smooth.
*Color*.—Upper surface at first opening: Near RHS Red-Purple N66C. Dotted near Red-Purple 53B. Under surface at first opening: Near RHS Red-Purple N66B. Inner surface at maturity: Near RHS Red-Purple 68A upper section dotted with Red-Purple 67A. Outer surface at maturity: Near RHS Red-Purple 68B. Upper surface at fading: Near RHS Red-Purple 68A upper section dotted with Red-Purple 70A. Under surface at fading: Near RHS Red-Purple 70B.

Bud:
*Shape*.—Elliptic.
*Length*.—2.5 cm.
*Diameter*.—1.5 cm.
*Color*.—Near RHS Red-Purple 71C.

Calyx/sepals:
*Quantity per flower*.—5 sepals.
*Shape*.—Narrow deltate.
*Length*.—0.7 cm.
*Width*.—0.4 cm.
*Apex*.—Acute.
*Base*.—Fused.
*Margin*.—Entire.
*Texture*.—Highly pubescent, hairs appressed.
*Color*.—Inner Surface: Near RHS Green 137C. Outer Surface: Near RHS Green 137A.

REPRODUCTIVE ORGANS

Stamens:
*Number*.—5, occasionally 7. fused to petaloids at irregular lengths. Some stamens fully-fused, with only anther unfused, some stamens 10% fused to petaloids.
*Stamen length*.—Average range 2.5 to 3.5 cm.
*Width*.—0.1 cm.
*Color*.—Near RHS Red-Purple N57B.
*Anthers*.—Length: Approximately 0.2 cm. Color: Near RHS Red-Purple 59A. Pollen: Not observed.

Pistil:
*Number*.—1.
*Length*.—Average range 4.0 cm to 5.5 cm.
*Style*.—Length: Average 3.7 cm to 5.0 cm. Color: Near RHS Red-Purple N66A.
*Stigma*.—Globular, colored near Red-Purple 59A.
*Ovary*.—Sericeous texture. Approximately 0.4 cm in diameter. Colored near Yellow-Green 145C.

OTHER CHARACTERISTICS

Disease and pest resistance: Not observed to be susceptible nor resistant to normal diseases and pests of *Rhododendron*.
Temperature tolerance: Observed hard to USDA Zone 7, presumed hardy to Zone 6.
Fruit/seed production: Not observed to date.

What is claimed is:

1. A new and distinct cultivar of *Rhododendron* plant named 'BAILEB' as herein illustrated and described.

* * * * *